(12) United States Patent
Cornish et al.

(10) Patent No.: US 8,138,196 B2
(45) Date of Patent: Mar. 20, 2012

(54) ANTIFUNGAL WALLBOARDS AND BUILDING MATERIALS AND METHODS FOR THE PRODUCTION THEREOF

(75) Inventors: Alexander Cornish, Basel (CH); Anja Greiner, Weinheim (DE); John R. James, Greensboro, NC (US); Gertrude Knauf-Beiter, Stein (CH); Johann Steiner, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 958 days.

(21) Appl. No.: 11/917,167

(22) PCT Filed: Jun. 13, 2006

(86) PCT No.: PCT/GB2006/002167
§ 371 (c)(1),
(2), (4) Date: Jun. 5, 2008

(87) PCT Pub. No.: WO2006/134347
PCT Pub. Date: Dec. 21, 2006

(65) Prior Publication Data
US 2008/0280929 A1  Nov. 13, 2008

Related U.S. Application Data

(60) Provisional application No. 60/690,403, filed on Jun. 14, 2005.

(51) Int. Cl.
*A01N 43/54* (2006.01)
*E04C 2/26* (2006.01)

(52) U.S. Cl. ........................ 514/269; 52/309.3
(58) Field of Classification Search .................. None
See application file for complete search history.

(56) References Cited

U.S. PATENT DOCUMENTS

| | | | |
|---|---|---|---|
| 6,194,463 B1 * | 2/2001 | Zeller | 514/607 |
| 6,767,647 B2 * | 7/2004 | Swofford et al. | 428/537.7 |
| 2003/0050194 A1 * | 3/2003 | Hopkinson et al. | 504/363 |
| 2007/0149694 A1 * | 6/2007 | Krishnan | 524/543 |
| 2008/0280929 A1 * | 11/2008 | Cornish et al. | 514/269 |

FOREIGN PATENT DOCUMENTS

| | | |
|---|---|---|
| WO | 0201955 | 1/2002 |
| WO | 0248100 | 6/2002 |
| WO | 03045147 | 6/2003 |
| WO | 03104583 | 12/2003 |
| WO | 2005051081 | 6/2005 |

* cited by examiner

*Primary Examiner* — Shanon A Foley
(74) *Attorney, Agent, or Firm* — William A. Teoli, Jr.

(57) ABSTRACT

The present invention relates to, inter alia, methods for the treatment of wallboards and the treated wallboards. In particular, the invention relates to the treatment of wallboards with a fungicidally effective amount of a strobilurin or strobilurin-type fungicide. In a particular embodiment the fungicide is azoxystrobin. The invention also provides for the treatment of wallboards and building materials with combinations of fungicides present in synergistic amounts.

6 Claims, No Drawings

ANTIFUNGAL WALLBOARDS AND BUILDING MATERIALS AND METHODS FOR THE PRODUCTION THEREOF

This application is a 371 of International Application No. PCT/GB2006/002167 filed Jun. 13, 2006, which claims priority to U.S. Ser. No. 60/690,403 filed Jun. 14, 2005, the contents of which are incorporated herein by reference.

The present invention relates to methods for the treatment of wallboards and the treated wallboards. In particular, the invention relates to the treatment of wallboards with a fungicidally effective amount of a strobilurin or strobilurin-type fungicide. More specifically, the fungicide is azoxystrobin. More specifically, the treatment comprises a fungicidally effective amount of a strobilurin, such as azoxystrobin, or strobilurin-type fungicide and a further fungicide such as one selected from the group consisting of: thiabendazole, fludioxonil, propiconazole and difenoconazole.

The fungi of relevance to the invention are those which are capable of growing on building materials such as wallboards. Fungi are versatile organisms and the substrate on which they grow can include building materials since such materials can be made of, or have applied to them, substances which support fungal growth. Fungal growth generally requires dampness, that can be caused on building materials by, for example, internal water leaks or external leaks, or by areas of high humidity or condensation. Fungal growth also requires a food source which, in this case, can be the building material itself or can be dirt or other nutritious material present on the building material.

Fungi which are capable of growing on building materials such as wallboards have been problematic for some time. Obvious effects of such fungi are discoloration of the material on which they grow, often accompanied by unpleasant smells. Fungi also contribute to the physical destruction of the material. In recent years, such fungi have also been an increasing cause for concern in relation to human health. Various health problems have been attributed to such fungi with most common being allergic reactions and in some cases, human infection. Certain fungi which are capable of growing on such building materials are also thought to be carcinogenic. Clearly these fungi are perceived as a growing threat to humans.

We have now found that certain fungicides, that were previously known for agricultural use, are surprisingly effective against fungi that are capable of growing on/infesting building materials such as wallboards. Agricultural use means application to crop plants or harvested agricultural products such as seeds. This invention represents a significant step forward in fungal control on building materials, in particular wallboards.

According to the present invention there is provided a method for the prevention and/or treatment of growth and/or infestation of a fungus on a wallboard comprising treating said wallboard with a fungicidally effective amount of a strobilurin or strobilurin-type fungicide.

Strobilurin and strobilurin-type fungicides are a well-known class of fungicides that act by inhibiting mitochondrial respiration by blocking electron transfer between cytochrome b and cytochrome c1 at the ubiquinol oxidising site. They include the methoxyacrylate strobilurins such as azoxystrobin and picoxystrobin, the oximinoacetate strobilurins such as kresoxim-methyl and trifloxystrobin, the oximinoacetamide strobilurins such as dimoxystrobin, metominostrobin, orysastrobin (BAS 520) and the strobilurin of the formula:

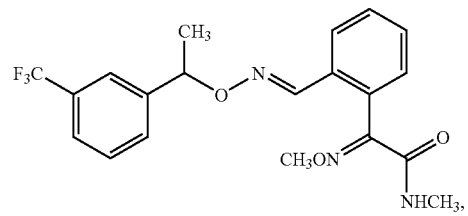

the dihydrodioxazine strobilurins such as fluoxastrobin, the methoxycarbamate strobilurins such as pyraclostrobin, the strobilurin of the formula:

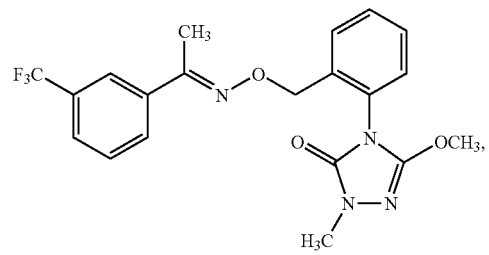

the imidazolinones strobilurin-types such as fenamidone, and the oxazolidinedione strobilurin-types such as famoxadone. Of particular interest is azoxystrobin. Azoxystrobin is also described as entry 47 in The Pesticide Manual, Thirteenth Edition, published by The British Crop Protection Council, 2003. Picoxystrobin is also described in the Pesticide Manual as entry 647.

Wallboard (also sometimes known as drywall or plasterboard) is a building material commonly used to make the internal dividing walls of buildings. Buildings include residential buildings such as houses and flats and commercial buildings such as shops, warehouses, hotels and factories and the like, also institutional buildings such as colleges. Wallboard includes ceiling board which is material used for internal ceilings. Wallboard is generally in the form of a flat sheet between 0.5 and 2 cm thick and comprises, usually, a gypsum core, usually coated on both sides, with paper. Wallboard is usually fixed to a wooden frame to form an internal wall, or fixed to ceiling spars to form an internal ceiling. Wallboard has many desirable properties, such as being relatively light and easy to cut, and having a surface that is easily decorated with paint or wallpaper. However, wallboard suffers from a particular problem if it is exposed to water and for that reason its use is restricted to internal areas of buildings. Gypsum is very water-absorbent, and once wet can take a long time to dry out. The combination of a damp gypsum core and the starch and cellulose in the paper on the surface provide an ideal substrate for fungi to grow. Essentially, the damp gypsum provides a convenient sustained water reservoir for the fungus while the paper provides nutrition. Even when used internally, wallboards can be exposed to water for example from leaky internal plumbing or from rainwater leaks from the outside of the building, or from sustained high humidity or condensation. Such leaks are unfortunately rather common and so fungal growth on wallboards is a continuing problem.

Fungi are at least in part responsible for so-called 'black mould', a fungal infestation of buildings. Wallboard is particularly susceptible to black mould, which has become a significant problem in buildings in some areas, and which has been blamed for a range of human health problems. Fungi are also responsible for facilitating discoloration of the material on which they grow and are a particular problem in residential buildings.

In a further aspect of the invention there is provided a method for the prevention and/or treatment of growth and/or infestation of a fungus on a wallboard comprising treating said wallboard with a fungicidally effective amount of a composition which comprises as active ingredients, synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof.

We have also identified that surprisingly fludioxonil synergises the activity of strobilurin/strobilurin-type fungicides and thiabendazole and in particular mixtures of azoxystrobin and thiabendazole against certain fungi. More specifically, the addition of small amounts of fludioxonil can powerfully increase the antifungal activity of particular fungicides against particular fungi that are deleterious to wallboards and other materials including building materials, paper, woods and plastics.

Fludioxonil is listed as entry 368 The Pesticide Manual, Thirteenth Edition, published by The British Crop Protection Council, 2003. Fludioxonil is mainly known as a fungicide for use on crops and also as a seed treatment. Thiabendazole is listed as entry 790, difenoconazole is listed as entry 247 and propiconazole is listed as entry 675.

In a particular embodiment the present invention describes and uses a mixture of azoxystrobin and thiabendazole wherein these compounds are present in synergistic amounts. In a further embodiment the present invention describes and uses a mixture of azoxystrobin, thiabendazole and fludioxonil wherein these compounds are present in synergistic amounts.

In a further embodiment said strobilurin fungicide is azoxystrobin. In a further embodiment said strobilurin fungicide is picoxystrobin.

The present invention still further provides a method as described above wherein the fungus is selected from the group consisting of: *Alternaria* sp.; *Penicillium* sp.; *Aspergillus* sp.; *Aureobasidium* sp.; and *Stachybotrys* sp.

In a particular embodiment the fungus is *Stachybotrys atra*. Throughout this specification *Stachybotrys atra* is interchangeable with *Stachybotrys chartarum*. In a further embodiment the fungus is *Alternaria tenuissima*. In a still further embodiment the fungus is *Penicillium chrysogeizum*. In a still further embodiment the fungus is *Aspergillus niger*. In a still further embodiment the fungus is *Aspergillus versicolor*. In a still further embodiment the fungus is *Aureobasidium pullulans*. In a still further embodiment the fungus is a combination of those mentioned above, in particular *Alternaria tenuissima*, *Penicillium chrysogenum*, *Aspergillus niger* and *Aspergillus versicolor*. In a still further embodiment the fungus is *Aureobasidium pullulans* and *Stachybotrys chartarum*.

Examples of other problematic fungi are: *Alternaria alternata, Aspergillus flavus, Aspergillus terreus, Aspergillus fumigatus, Aspergillus repens, Aspergillus veisicolor, Candida albicans, Chaetomium globosum, Cladosporium cladosporioides, Cladosporium herbaruin, Cladosporium sphaerospermum, Coniophora puteana, Curvularia geniculata, Diplodia natalensis, Epidermophyton floccosum, Fusarium oxysporum, Gliocladium virens, Gloeophyllum trabeum, Humicola grisea, Lecythophora mutabilis, Lentinus cyathiformis, Lentinus lepidus, Memnionella echinata, Mucor indicus, Mucor racemosus, Oligoporus placenta, Paecilomyces variotii, Penicillium citrinum, Penicillium funiculosum, Penicillium ochrochloron, Penicillium purpurogenum, Penicillium pinophilum, Penicillium variabile, Petriella setifera, Phanerochaete chrysosporium, Phoma violacea, Poria placenta, Rhodotorula rubra, Schizophyllum commune, Sclerophoma phytiophila Scopulariopsis brevicaulis, Serpula laciymans, Sporobolomyces roseus, Stemphylium dendriticum, Trichophyton mentagrophytes, Trichurus spiralis, Trichophyton rubrum, Ulocladium atrum* and *Ulocladium chartarum*.

Of particular concern are: *Alternaria alternata, Alternaria tenuissima, Aspergillus niger, Aspergillus versicolor, Aureobasidium pullulans, Chaetomium globosum, Cladosporium cladosporioides, Coniophora puteana, Gloeophyllum trabeum, Memnionella echinata, Mucor indicus, Oligoporus placenta, Penicillium citrinum, Penicillium chrysogenum, Penicillium funiculosum, Penicillium pinophilum, Sclerophoma phytiophila, Stachybotrys atra, Stachybotrys chartarum*, and *Ulocladium chartarum*.

The present invention still further provides a method as described above wherein said wallboard is treated during the manufacturing process of said wallboard.

The present invention still further provides a method as described above wherein said fungicide or fungicides is/are included in the gypsum core of said wallboard.

The present invention still further provides a method as described above in which the fungicide or fungicides is/are applied to the surface of the gypsum core of the wallboard.

The present invention still further provides a method as described above wherein the fungicide or fungicides is/are included in the paper coating of the wallboard.

The present invention still further provides a method as described above wherein the fungicide or fungicides is/are included in the paper during the papermaking process.

The present invention still further provides a method as described above wherein the fungicide or fungicides is/are applied to the paper after said paper has been made.

The present invention still further provides a method as described above wherein the substantially finished wallboard is treated with the fungicide or fungicides.

The present invention still further provides a method as described above wherein the wallboard is treated with the fungicide or fungicides prior to installation of said wallboard.

The present invention still further provides a method as described above wherein the wallboard is treated with the fungicide or fungicides after installation of said wallboard.

Treating the finished wallboard can be carried out as part of its manufacture or in a separate process, for example in a separate treatment plant, or on or near the building site where the wallboard is to be installed.

The treatment can be carried out by a number of methods including those mentioned within this specification relating to the treatment of building materials. In particular, brushing, wiping, rolling or preferably spraying the surface with a composition containing the fungicide/fungicides of the invention. If infestation with fungi is already apparent or suspected then the application of the fungicide/fungicides can be preceded by a washing step using either conventional cleaning materials such as bleach and/or detergents to remove some or all of the visible mould or staining. Wallboard that was originally treated from new in accordance with the invention can also be retreated by any of these methods, for example to increase or prolong the fungicidal effect. This retreatment and the process therefor, also form part of the present invention.

In a still further aspect of the present invention there is provided a method for the prevention and/or treatment of fungal contamination on a wallboard comprising treating said wallboard with a fungicidally effective amount of a strobilurin or strobilurin-type fungicide.

In a still further aspect of the invention there is provided a method for the prevention and/or treatment of fungal contamination on a wallboard comprising treating said wallboard with a fungicidally effective amount of a composition which comprises as active ingredients, synergistic amounts of: (a) a strobilurin or strobilurin-type fungicide and
(b) a fungicide selected from the group consisting of: (bi) thiabendazole; (bii) difenoconazole; (biii) propiconazole; (biv) fludioxonil or a combination thereof.

The present invention still further provides a method as described above wherein said strobilurin fungicide is azoxystrobin. In a particular embodiment said wallboard is treated with a composition of azoxystrobin and thiabendazole wherein these compounds are present in synergistic amounts. In a further embodiment said wallboard is treated with a composition of azoxystrobin, thiabendazole and fludioxonil wherein these compounds are present in synergistic amounts.

The treatment can be preventative, that is it can be carried out before there is visible fungal growth, or it can be curative, that is it can be carried out on wallboard on which fungus is already growing.

The present invention still further provides a wallboard obtainable by a method as described above.

The present invention still further provides a wallboard obtained by a method as described above.

In a further aspect of the invention there is provided a wallboard that has been treated with a fungicidally effective amount of a strobilurin or strobilurin-type fungicide.

In a still further aspect of the invention there is provided a wallboard that has been treated with a fungicidally effective amount of a composition which comprises as active ingredients: synergistic amounts of: (a) a strobilurin or strobilurin-type fungicide and
(b) a fungicide selected from the group consisting of: (bi) thiabendazole; (bii) difenoconazole; (biii) propiconazole; (biv) fludioxonil or a combination thereof.

The present invention still further provides a wallboard as described above wherein said strobilurin fungicide is azoxystrobin. In a further embodiment of the invention said strobilurin fungicide is picoxystrobin.

The present invention still further provides a wallboard as described above wherein the fungicides are azoxystrobin and thiabendazole. In a further embodiment the fungicides are azoxystrobin, thiabendazole and fludioxonil.

The present invention still further provides a wallboard as described above wherein the fungicide or fungicides is/are included in the gypsum core. There are a number of ways to achieve this. For example the fungicide/fungicides can be included in the gypsum core by mixing it with the gypsum before said gypsum hardens.

The present invention still further provides a wallboard as described above wherein the fungicide or fungicides is/are applied to the surface of the gypsum core of the wallboard.

The present invention still further provides a wallboard as described above wherein the fungicide or fungicides is/are included in the paper coating of the wallboard.

The present invention still further provides a wallboard as described above wherein the fungicide or fungicides is/are applied after the wallboard is made.

In a still further aspect of the invention there is provided a wallboard treated with a fungicidally effective amount of a strobilurin or strobilurin-type fungicide such that growth of fungi on said wallboard is prevented.

In a still further aspect of the invention there is provided a wallboard treated with a fungicidally effective amount of a composition which comprises as active ingredients, synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof, such that growth of fungi on said wallboard is prevented. In a particular embodiment said composition comprises as active ingredients (a) azoxystrobin and (bi) thiabendazole in such synergistic amounts. In a further embodiment said composition comprises as active ingredients (a) azoxystrobin, (bi) thiabendazole and (biv) fludioxonil in such synergistic amounts.

In a still further aspect of the invention there is provided a method for re-treating a previously treated wallboard comprising applying to said wallboard a fungicidally effective amount of a strobilurin or strobilurin-type fungicide such that fungal contamination of said wallboard is prevented and/or retarded.

In a still further aspect of the invention there is provided a method for treating a wallboard that has been previously treated with a different fungicide comprising applying to said wallboard a fungicidally effective amount of a strobilurin or strobilurin-type fungicide such that fungal contamination of said material is prevented and/or retarded.

Preferably the wallboard comprises a fungicide/fungicides according to the invention present in concentrations of about 50 ppm to 1000 ppm.

The composition containing the fungicide/fungicides according to the invention can be based on organic solvents or can be water based. Organic solvents can have the advantage of relatively quick drying, but water-based compositions are preferred because of their lower air pollution potential, and lower odour, particularly in buildings. One example of a suitable water-based composition is an emulsion concentrate.

The composition can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and other applicable formulations well known to the person skilled in the art.

Dustable powders (DP) may be prepared by mixing a fungicide/fungicides according to the invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a fungicide/fungicides with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water-soluble granules (SG).

Wettable powders (WP) may be prepared by mixing a fungicide/fungicides with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a fungicide/fungicides according to the invention and one or more powdered solid diluents or carriers, or from pre-formed blank granules by absorbing a fungicide/fungicides according to the invention (or a solution thereof, in a suitable agent) in a porous granular material (such as pumice, attapulgite clays, fuller's earth, kieselguhr, diatomaceous earths or ground corn cobs) or by adsorbing a fungicide/fungicides according to the invention (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a fungicide/fungicides according to the invention in water or an organic solvent, such as a ketone, alcohol or glycol ether. These solutions may contain a surface-active agent (for example to improve water dilution or prevent crystallisation in a spray tank).

Emulsifiable concentrates (EC) or oil-in-water emulsions (EW) may be prepared by dissolving a fungicide/fungicides according to the invention in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a fungicide/fungicides according to the invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A fungicide/fungicides according to the invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a fungicide/fungicides according to the invention. SCs may be prepared by ball or bead milling a fungicide/fungicides according to the invention in a suitable medium, optionally with one or more dispersing agents, to produce a fine particle suspension of the compound. One or more wetting agents may be included in the composition and a suspending agent may be included to reduce the rate at which the particles settle. In a particular embodiment of the invention there is provided a mixture of (azoxystrobin) Amistar® and (thiabendazole) Tecto® or Mertect®. Alternatively, a fungicide/fungicides according to the invention may be dry milled and added to water, containing agents hereinbefore described, to produce the desired end product.

Aerosol formulations comprise a fungicide/fungicides according to the invention and a suitable propellant (for example n-butane). A fungicide/fungicides according to the invention may also be dissolved or dispersed in a suitable medium (for example water or a water miscible liquid, such as n-propanol) to provide compositions for use in non-pressurised, hand-actuated spray pumps.

A fungicide/fungicides according to the invention may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a fungicide/fungicides according to the invention and, optionally, a carrier or diluent therefor. The polymeric shell may be produced by either an interfacial polycondensation reaction or by a coacervation procedure. The compositions may provide for controlled release of a fungicide/fungicides according to the invention. A fungicide/fungicides according to the invention may also be formulated in a biodegradable polymeric matrix to provide a slow, controlled release of the compound.

The composition may include one or more additives to improve the properties of the composition (for example by improving wetting, retention or distribution on surfaces; or absorption into surfaces). Such additives include surface-active agents, spray additives based on oils, for example certain mineral oils or natural plant oils (such as soy bean and rape seed oil), and blends of these with other bio-enhancing adjuvants (ingredients which may aid or modify the action of a fungicide/fungicides according to the invention).

The compositions of this invention may contain other compounds having biological activity, for example compounds having similar or complementary fungicidal activity or which possess, insecticidal and/or acaricidal and/or algicidal activity. The fungicide can be combined with other fungicides. Combinations with other fungicides can be used to control a broader range of fungi, which is particularly useful if multiple species of fungi are present, or if the species is not known.

The addition of another active ingredient may provide a composition having a broader spectrum of activity or increased persistence at a locus, synergise the activity or complement the activity (for example by increasing the speed of effect or overcoming repellency) of a fungicide/fungicides according to the invention, or help to overcome or prevent the development of resistance to individual components.

Examples of fungicidal compounds which may be included in the composition of the invention are AC 382042 (N-(1-cyano-1,2-dimethylpropyl)-2-(2,4-dichlorophenoxy) propionamide), acibenzolar-5-methyl, alanycarb, aldimorph, anilazine, azaconazole, azafenidin, benalaxyl, benomyl, benthiavalicarb, biloxazol, bitertanol, blasticidin S, boscalid (new name for nicobifen), bromuconazole, Bronopol, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquino-late, copper sulphate, copper tallate, and Bordeaux mixture, cyamidazo-sulfamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenzoquat, diflumetorim, diiodomethyl-p-tolylsulfone (Amical, from Dow) O,O-di-iso-propyl-5-benzyl thiophosphate, dimefluazole, dimetconazole, dimethirimol, dimethomorph, dimoxystrobin, diniconazole, dinocap, dithianon, Dithiocarbamates, dodecyl dimethyl ammonium chloride, dodemorph, dodine, doguadine, edifenphos, epoxiconazole, ethaboxam, ethirimol, ethyl (Z)-N-benzyl-N([methyl(methyl-thioethylideneaminooxycarbonyl) amino]thio)-β-alaninate, etridiazole, famoxadone, fenamidone, fenarimol, fenbuconazole, fenfuram, fenhexamid, fenoxanil (AC 382042), fenpropidin, fenpropimorph, fentin acetate, fentin hydroxide, ferbam, ferimzone, fluazinam, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, 3-iodo-2-propynyl butylcarbamate (IBPC), ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, MBT mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, 2-O-octyl-4-isothiazolin-3-one (Skane M 8 Rohm& Hass), ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propineb, propionic acid, proquinazid, prothioconazole, pyraclostrobin, pyrazophos, Sodium and Zinc Pyrithione (Omadine chemistry from Arch Chem.), pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thifluzamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

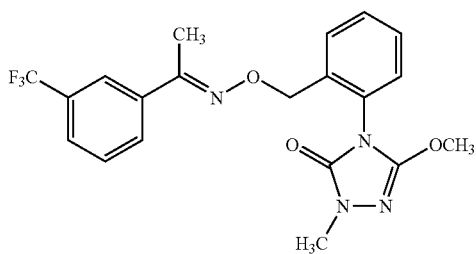

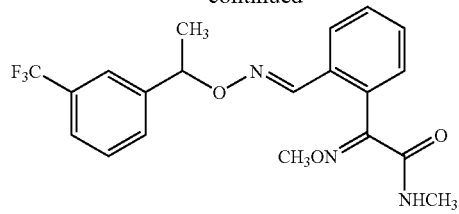

In a still further aspect of the invention there is provided a mixture for use in the present invention which mixture comprises as active ingredients (a) a strobilurin or strobilurin-type fungicide and (b) thiabendazole and (c) propiconazole wherein said ingredients are present in synergistic amounts.

In a still further aspect of the invention there is provided a mixture for use in the present invention which mixture comprises as active ingredients (a) a strobilurin or strobilurin-type fungicide and (b) fludioxonil and (c) propiconazole wherein said ingredients are present in synergistic amounts.

In a still further aspect of the invention there is provided a mixture for use in the present invention which mixture comprises (a) a strobilurin or strobilurin-type fungicide and (b) difenoconazole and (c) thiabendazole wherein the fungicides are present in synergistic amounts.

In a still further aspect of the invention there is provided a mixture for use in the present invention which mixture comprises (a) a strobilurin or strobilurin-type fungicide and (b) difenoconazole and (c) fludioxonil wherein the fungicides are present in synergistic amounts.

In a still further aspect of the invention there is provided a mixture for use in the present invention which mixture comprises (a) a strobilurin or strobilurin-type fungicide and (b) thiabendazole and (c) fludioxonil wherein the fungicides are present in synergistic amounts.

In a still further aspect of the invention there is provided a mixture for use in the present invention which mixture comprises (a) a strobilurin or strobilurin-type fungicide and (b) difenoconazole and (c) propiconazole wherein the fungicides are present in synergistic amounts.

In a still further aspect of the invention there is provided a mixture for use in the present invention which mixture comprises (a) a strobilurin or strobilurin-type fungicide and (b) propiconazole wherein the fungicides are present in synergistic amounts.

In a still further aspect of the invention there is provided a mixture for use in the present invention which mixture comprises (a) a strobilurin or strobilurin-type fungicide and (b) fludioxonil wherein the fungicides are present in synergistic amounts.

In a still further aspect of the invention there is provided a mixture for use in the present invention which mixture comprises (a) a strobilurin or strobilurin-type fungicide and (b) difenoconazole wherein the fungicides are present in synergistic amounts.

In a particular embodiment said strobilurin fungicide is azoxystrobin.

Some mixtures may comprise active ingredients that have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

A dye can also be included in the compositions. This can be useful to differentiate treated wallboard from untreated wallboard. When the wallboard is new this provides a simple visual identifier for warehouse operators and construction workers. A dye can also be useful when the composition is applied to wallboard that has already been installed to identify those areas to which fungicide has been applied, for example when spraying a large area. It is useful for the applicators to see where they have applied the composition particularly when multiple operators are carrying out the application, or when the application process carried out over a number of days. It also allows easy inspection so that supervisors and surveyors can see what has been treated. It is also possible to use the depth of the colour as a guide to the amount of fungicide applied, particularly when it is applied to the wallboard surface. The depth of colour can be assessed visually, or a calorimeter can be used.

The present invention still further provides a building comprising a wallboard as described above. In a particular embodiment said building is a temporary building. In a further embodiment said building is a permanent structure. In a still further embodiment said building comprises a plurality of wallboards as described above.

In a still further aspect of the invention there is provided the use of a fungicidally effective amount of a strobilurin or strobilurin-type fungicide in a method of controlling fungal growth on a wallboard.

In a still further aspect of the invention there is provided the use of a fungicidally effective amount of a composition which comprises as active ingredients synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof in a method of controlling fungal growth on a wallboard.

In a still further aspect of the invention there is provided the use of a fungicidally effective amount of a strobilurin or strobilurin-type fungicide in the production of a fungicidally treated wallboard.

In a still further aspect of the invention there is provided the use of a fungicidally effective amount of a composition which comprises as active ingredients, synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof in the production of a fungicidally treated wallboard.

The present invention still further provides the use as described above wherein said strobilurin fungicide is azoxystrobin. In a still further embodiment, the present invention provides for the use as described above wherein said strobilurin fungicide is picoxystrobin.

In a still further aspect of the invention there is provided a kit comprising a fungicidally effective amount of a strobilurin or strobilurin-type fungicide and a wallboard and a means for applying said fungicide to said wallboard.

In a still further aspect of the invention there is provided a kit comprising a fungicidally effective amount of a synergistic composition which comprises as active ingredients: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof and a wallboard and a means for applying the fungicides to said wallboard.

In a still further aspect of the invention there is provided a kit comprising a fungicidally effective amount of azoxystrobin and a wallboard and a means for treating said wallboard with said azoxystrobin.

In a still further aspect of the invention there is provided a kit comprising a fungicidally effective amount of azoxystrobin and thiabendazole and a wallboard and a means for treating said wallboard with said azoxystrobin and said thiabendazole.

In a still further aspect of the invention there is provided a composition suitable for use in the treatment of a wallboard comprising as active ingredients synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof. In a particular embodiment said composition comprises azoxystrobin and thiabendazole. In a further embodiment said composition comprises azoxystrobin, thiabendazole and fludioxonil.

In a still further aspect of the invention there is provided a composition suitable for use in the treatment of a wallboard consisting of, synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof and a fungicidally acceptable carrier and/or adjuvant. In a particular embodiment said composition consists of azoxystrobin and thiabendazole and a fungicidally acceptable carrier and/or adjuvant. In a further embodiment said composition consists of azoxystrobin, thiabendazole and fludioxonil and a fungicidally acceptable carrier and/or adjuvant.

In a still further aspect of the invention there is provided a method for protecting wood from infestation with *Coniophora puteana* comprising treating said wood with a strobilurin or strobilurin-type fungicide.

In a still further aspect of the invention there is provide a method for the prevention of fungal infection induced wet-rot in wood comprising treating said wood with a strobilurin or strobilurin-type fungicide.

In a still further aspect of the invention there is provided a method for the prevention and/or treatment of *Coniophora puteana* growth/infestation on wood comprising treating said wood with a fungicidally effective amount of a strobilurin or strobilurin-type fungicide The present invention further provides a method as described above wherein said strobilurin fungicide is azoxystrobin.

The present invention still further provides a method as described above wherein said treatment additionally comprises treatment with a fungicide selected from the group consisting of: (bi) thiabendazole; (bii) difenoconazole; (biii) propiconazole; (biv) fludioxonil or a combination thereof.

In a still further aspect of the invention there is provided a composition comprising as active ingredients, synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof. In a particular embodiment said composition comprises azoxystrobin and thiabendazole. In a further embodiment said composition comprises azoxystrobin, thiabendazole and fludioxonil.

In a still further aspect of the invention there is provided a composition consisting of synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof and a fungicidally acceptable carrier and/or adjuvant. In a particular embodiment said composition consists of azoxystrobin and thiabendazole and a fungicidally acceptable carrier and/or adjuvant. In a further embodiment said composition consists of azoxystrobin, thiabendazole and fludioxonil and a fungicidally acceptable carrier and/or adjuvant.

In a still further aspect of the invention there is provided a composition suitable for use in the treatment of a wallboard comprising as active ingredients, synergistic amounts of: (a) a strobilurin or strobilurin-type fungicide and (b) thiabendazole.

In a still further aspect of the invention there is provided a composition suitable for use in the treatment of a wallboard consisting of synergistic amounts of: (a) a strobilurin or strobilurin-type fungicide and (b) thiabendazole and a fungicidally acceptable carrier and/or adjuvant. In a particular embodiment said composition consists of azoxystrobin, thiabendazole and fludioxonil and a fungicidally acceptable carrier and/or adjuvant.

In a still further aspect of the invention there is provided a composition suitable for use in the treatment of wood comprising a fungicidally effective amount of a composition which comprises as active ingredients, synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof.

In a still further aspect of the invention there is provided a composition suitable for use in the treatment of wood consisting of synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof and a carrier and/or adjuvant.

The present invention still further provides a composition as described above wherein said strobilurin fungicide is azoxystrobin.

Suitable carriers and adjuvants may be solid or liquid and are, for example, natural or regenerated mineral substances, solvents, dispersants, wetting agents, tackifiers, thickeners, binders or fertilisers. They are conveniently formulated in known manner to form, for example, emulsifiable concentrates, coatable pastes, directly sprayable or dilutable solutions, dilute emulsions, wettable powders, soluble powders, dusts, granules or capsules, for instance by encapsulation in polymers substances. As with the nature of the composition, the method of application, such as spraying, atomising, dusting, scattering, coating or pouring, is chosen in accordance with the prevailing circumstances.

The formulations may be prepared in known manner, typically by intimately mixing, grinding and/or extruding the fungicide/fungicides according to the invention with an extender, for example, a solvent or a solid or liquid carrier and, where appropriate, one or more surface-active compounds (surfactants).

In a still further aspect of the invention there is provided a method for the prevention and/or treatment of fungal growth/infestation on paper comprising treating said paper with a composition which comprises as active ingredients synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof. In a particular embodiment said composition comprises azoxystrobin and thiabendazole. In a further embodiment said composition comprises azoxystrobin, thiabendazole and fludioxonil.

In a still further aspect of the invention there is provided a paper product comprising a composition which comprises as active ingredients synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof. In a particular embodiment said composition comprises azoxystrobin and thiabendazole. In a further embodiment said composition comprises azoxystrobin, thiabendazole and fludioxonil.

In a still further aspect of the invention there is provided a paper product comprising, as active ingredients, synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof. In a particular embodiment said paper product comprises azoxystrobin and thiabendazole. In a further embodiment said paper product comprises azoxystrobin, thiabendazole and fludioxonil.

In a still further aspect of the invention there is provided a method for the prevention and/or treatment of fungal growth/infestation in a heat exchange system comprising treating said system with a composition which comprises as active ingredients synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof. In a particular embodiment said composition comprises azoxystrobin and thiabendazole. In a further embodiment said composition comprises azoxystrobin, thiabendazole and fludioxonil.

In a still further aspect of the invention there is provided a cooling lubricant comprising a composition which comprises as active ingredients synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof. In a particular embodiment said composition comprises azoxystrobin and thiabendazole. In a further embodiment said composition comprises azoxystrobin, thiabendazole and fludioxonil.

The synergistic fungicidal mixtures of the present invention may also be used in the protection and/or treatment of cooling and heating systems, ventilation and air conditioning systems and parts of production plants, for example cooling-water circuits.

The synergistic composition may be applied to the material referred to above in a manner as described above and the fungicides may be applied in a ratio as defined in the examples.

In a still further aspect of the invention there is provided a method for the prevention and/or treatment of fungal growth/infestation on a building material comprising treating said material with a fungicidally effective amount of a strobilurin or strobilurin-type fungicide.

In a still further aspect of the invention there is provided a method for the prevention and/or treatment of fungal growth/infestation on a building material comprising treating said material with a fungicidally effective amount of a composition which comprises as active ingredients synergistic amounts of: (a) a strobilurin or strobilurin-type fungicide and (b) a fungicide selected from the group consisting of: (bi) thiabendazole; (bii) difenoconazole; (biii) propiconazole; (biv) fludioxonil or a combination thereof. In a particular embodiment said composition comprises azoxystrobin and thiabendazole. In a further embodiment said composition comprises azoxystrobin, thiabendazole and fludioxonil. The synergistic composition may be applied to the building material in a manner as described above and the fungicides may be applied in a ratio as defined in the examples.

In a particular embodiment of the invention said strobilurin or strobilurin-type fungicide is azoxystrobin.

"building material" means those materials used for construction and the like. In particular, building material includes structural timber, doors, cupboards, storage units, carpets, particularly natural fibre carpets such as wool and hessian, paints, plastics, wood (including engineered wood) and wood plastic composite. In addition to this, building material includes adhesives, sealants, joining materials and joints and insulation material. In a particular embodiment "building material" means structural timber. In a further embodiment "building material" means engineered wood. In a further embodiment "building material" means plastic. Plastics includes plastic polymers and copolymers, including: acrylonitrile butadiene styrene, butyl rubber, epoxies, fluoropolymers, isoprene, nylons, polyethylene, polyurethane, polypropylene, polyvinyl chloride, polystyrene, polycarbonate, polyvinylidene fluoride, polyacrylate, polymethyl methacrylate, polyurethane, polybutylene, polybutylene terephthalate, polyether sulfone, polyphenyllenoxide, polyphenylene ether, polyphenylene sulfide, polyphtatamide, polysulphene, polyester, silicone, styrene butadiene rubber and combinations of polymers. In a further embodiment "building material" means polyvinyl chloride (PVC). In a further embodiment "building material" means polyurethane (PU). In a further embodiment "building materials" means paint. In a further embodiment "building material" means wood plastic composite (WPC). Wood plastic composite is a material that is well known in the art. A review of WPCs can be found in the following publication—Craig Clemons—Forrest Products Journal. June 2002 Vol 52. No. 6. pp 10-18.

"Wood" is to be understood as meaning wood and wood products, for example: derived timber products, lumber, plywood, chipboard, flakeboard, laminated beams, oriented strandboard, hardboard, and particleboard, tropical wood, structural timber, wooden beams, railway sleepers, components of bridges, jetties, vehicles made of wood, boxes, pallets, containers, telegraph-poles, wooden fences, wooden lagging, windows and doors made of wood, plywood, chipboard, joinery, or wooden products which are used, quite generally, for building houses or decks, in building joinery or wood products that are generally used in house-building including engineered wood, construction and carpentry.

The methods of the invention can be used in the prevention and/or treatment of the growth/infestation by/of a fungus as described within this specification. The fungus can be controlled by treating the fungus or the building material with a fungicide/synergistic composition according to the invention in a convenient manner. Examples of ways in which the fungus or building material can be treated with a fungicide according to the invention are: by including said fungicide in the building material itself, absorbing, impregnating, treating (in closed pressure or vacuum systems) said material with said fungicide, dipping or soaking the building material, or coating the building material for example by curtain coating, roller, brush, spray, atomisation, dusting, scattering or pouring application.

In a still further aspect of the invention there is provided a method for producing a treated building material comprising applying a fungicidally effective amount of the fungicide/fungicides according to the invention to said material such that fungal contamination of said material is prevented and/or retarded.

In a still further aspect of the invention there is provided a method for re-treating a treated building material comprising applying to said material a fungicidally effective amount of the fungicide/fungicides according to the invention such that fungal contamination of said material is prevented and/or retarded.

The present invention still further provides a building material obtainable by a method as described above.

In a still further aspect of the invention there is provided a building material treated with a fungicidally effective amount of a fungicide/fungicides according to the invention such that growth of fungi on said material is prevented.

The present invention still further provides a building comprising a building material as described above. In a particular embodiment said building is a temporary building. In a further embodiment said building is a permanent structure.

In a still further aspect of the invention there is provided the use of a fungicide/fungicides according to the invention in a method of treating a building material to prevent and/or treat growth and/or infestation of a fungus as described above on said material.

In a still further aspect of the invention there is provided a kit of parts comprising fungicide/fungicides according to the invention and a means for applying said fungicide/fungicides to a building material.

In a still further aspect of the invention there is provided a kit of parts comprising fungicide/fungicides according to the invention and a building material and a means for applying said fungicide/fungicides to said building material.

The present invention still further provides a method as described above wherein the fungi comprises *Coniophora puteana*. In a particular embodiment said method prevents and/or treats growth/infestation of *Coniophora puteana*. In a still further embodiment there is provided a method as described above wherein said fungicidally effective amount comprises an amount of fungicide that is capable of preventing and/or treating growth or infestation of *Coniophora puteana*.

In a particular embodiment the fungicide/fungicides may be applied by a means as described above. In particular, said fungicide may be applied by a means selected from: a roller, brush, spray, atomisation, means for dusting, scattering or pouring.

The invention will now be described with reference to the following examples:

EXAMPLES

Example 1

Wallboard paper samples treated with Azoxystrobin/thiabendazole using ASTM test method no. ASTM D 3273-00.

ASTM D 3273-00, Standard Test Method for Resistance to Growth of Mold on the Surface of Interior Coatings in an Environmental Chamber. ASTM International, 100 Barr Harbor Drive, PO Box C700, West Conshohocken, Pa. 19428-2959, United States. The method involves suspending paper sheets in an environmental chamber held at 32+/−1 degree Celsius at 95-98% relative humidity. The floor of the chamber holds a tray of soil that is inoculated with *Aureobasidium pullulans* (ATCC 9348), *Aspergillus niger* (ATCC 6275) & *Penicillium* sp (ATCC 9849) according to the method. The organisms sporulate in the soil and provide a continuous inoculum. Growth is rated after an appropriate time period (in this case 90 days) by visual assessment of surfaces compared to a set of photographic standards.

Table 1 below provides the average scores obtained. The application column relates to the rate of the active ingredients in pounds of active ingredient applied to the paper per ton of paper. The paper test samples are rated for defacement caused by fungal growth. The rating scale is from 0 to 10, where 0=complete defacement and 10=no defacement. Ratings were taken at 60, 90 and 120 days after inoculation.

TABLE 1

| | Application Rate lb active/ton paper | 60 Days | | 90 Days | | 120 Days | |
|---|---|---|---|---|---|---|---|
| Treatment | | Creamface Paper | Greyback Paper | Creamface Paper | Greyback Paper | Creamface Paper | Greyback Paper |
| Thiabendazole - Mertect ™ 340F | TBZ 0.1 | 6.00 | 7.67 | 4.00 | 8.00 | 5.00 | 9.00 |
| Thiabendazole - Mertect ™ 340F | TBZ 0.5 | 7.67 | 7.33 | 5.33 | 7.00 | 7.33 | 6.67 |
| Thiabendazole - Mertect ™ 340F | TBZ 1.0 | 9.00 | 8.00 | 8.67 | 7.67 | 10.00 | 9.67 |
| Thiabendazole - Mertect ™ 340F | TBZ 3.0 | 9.33 | 9.67 | 9.00 | 10.00 | 9.00 | 10.00 |
| Thiabendazole - Mertect ™ 340F | TBZ 5.0 | 9.33 | 9.33 | 8.33 | 9.00 | 9.00 | 10.00 |
| Azoxystrobin - Heritage ™ 50DF | AZO 0.1 | 9.00 | 10.00 | 7.33 | 10.00 | 7.00 | 10.00 |
| Azoxystrobin - Heritage ™ 50DF | AZO 0.5 | 8.67 | 10.00 | 8.33 | 9.67 | 8.67 | 10.00 |
| Azoxystrobin - Heritage ™ 50DF | AZO 1.0 | 9.33 | 10.00 | 9.00 | 8.67 | 9.00 | 10.00 |
| Azoxystrobin - Heritage ™ 50DF | AZO 3.0 | 9.67 | 10.00 | 8.33 | 8.33 | 8.67 | 10.00 |
| Azoxystrobin - Heritage ™ 50DF | AZO 5.0 | 9.33 | 10.00 | 8.33 | 9.00 | 8.00 | 10.00 |
| Thiabendazole/Azoxystrobin Mixture | TBZ/AZO 1.0/1.0 | 10.00 | 10.00 | 10.00 | 10.00 | 10.00 | 10.00 |

Example 2

Comparison of a strobilurin fungicide (azoxystrobin) against other fungicides;

1. Propagation

Stem cultures of *Coniophora puteana* were produced by propagating the fungus on a growth medium comprising yeast extract (10 g), glycerol (20 ml), magnesium sulphate (0.5 g), sodium nitrate (6.0 g), potassium chloride (0.5 g), potassium dihydrogen orthophosphate (1.5 g), agar (20 g) in distilled water (980 ml).

2. Test

Fungicides were added at levels of 5000, 100, 10, 1, 0.1 and 0.01 mg fungicide/litre of growth medium (described above) to give five different growth medium compositions for each fungicide. Mycelial plugs were taken from the stem cultures and transferred upside down onto petri dishes containing the fungicide amended agar.

3. Assessment

The radial mycelial growth of the fungus was measured individually on all test petri dishes. The results are expressed as % activity relative to the radial growth on agar without fungicide.

4. Analysis

For each fungicide, a graph was drawn of percentage activity against concentration of fungicide in the growth medium. From this graph, the concentrations of fungicide required to achieve 80% activity was estimated. These figures are given in the results table.

TABLE 2

Results
1. *Coniophora puteana* Results.

| Fungicide | Concentration required for 80% Activity in mg/l |
|---|---|
| Azoxystrobin | 0.38 |
| Propiconazole | 1.8 |
| Thiabendazole | >5000 |

Example 3

Mixtures of the strobilurin fungicide azoxystrobin with other fungicides.

The following compounds and formulations were used:

| Active Ingredient (ai) | Abbreviation | Formulation |
|---|---|---|
| Fludioxonil | FDL | SC230 |
| Propiconazole | PPZ | EC250 |
| Azoxystrobin | AZO | WG50 |
| Thiabendazole | TBZ | SC500 |
| Difenoconazole | DFZ | EC250 |

Compounds were tested at different rates, namely for test number 006-2005: (100, 50, 12.5, 3.1, 1.6, 0.8, 0.2, 0.05, 0 mg ai/l), and for test number 015-2005: 200, 100, 25, 12.5, 6.25, 3.12, 1.6, 0.8, 0.4, 0.2 mg/l Test organisms and media used:

| Organism | Cultivation of fungi | Test medium | Test conditions |
|---|---|---|---|
| All organisms | 24° C., on PDA medium | spore suspension in 0.3% AE media | Incubation at 24° C. for 3-6 days |

Propagation of the different fungi:

*Alternaria tenuissima* (DSM 63360), *Penicillium chrysogenum* (DSM 895), *Stachybotrys chartarum* (DSM2144), *Aspergillus niger* (DSM 63263), *Aspergillus versicolor* (DSM 1943) and *Aureobasidium pullulans* (ATCC 15233) were separately cultivated on PDA media to suppress sporulation. Spore suspensions were produced for each fungi. Spore concentrations of approx. 100.000 spores/ml were used.

Test method used: liquid culture assay on 24 well plates.

For solo (i.e. single) ai testing the formulated fungicide (100 ul) was filled into the 24 well plates and 100 ul distilled water was added. Afterwards 800 ul of 0.3% AE media was added to the plate. The spore suspension of the specific fungi was added to this media in advance containing approx. 100,000 spores/ml. The 24 well plates were sealed and incubated at 24° C.

Dependent on the growth properties of each organisms, the evaluation was done after 3 to 6 days, when the surface of the check well was covered with mycelium. The evaluation was performed by assessing the growth of the fungi related to the check growth. The results are expressed as % activity relative to the check (values of 0-100% growth). Afterwards the results were converted in % O growth inhibition.

For synergism testing of the 2-way mixtures 100 ul of each fungicide were filled into 24 well plates and 800 ul of 0.3% AE media containing the spore suspension was added. Different ratios of the 2 fungicide rates were tested at the same time.

Analysis:

For the mixtures of different fungicides the synergism was calculated based on the Colby equation, which is described below:

A synergistic effect exists whenever the action of the active ingredient combination of the compound of formula I and one or more compounds of formula II is greater than the sum of the actions of the active ingredients applied individually.

The fungicidal action to be expected, We, for a given combination of two fungicides can be calculated as follows (see COLBY, S. R. "Calculating synergistic and antagonistic response of herbicide combinations". Weeds 15, pages 20-22; 1967):

$$We = X + [Y \times (100 - X)/100]$$

wherein:

X=% activity in the case of treatment with the compound of formula I at rate x, in comparison with untreated control (=0%).

Y=% activity in the case of treatment with a compound of formula II at rate y, in comparison with untreated control.

We=expected activity (% activity in comparison with untreated control) after treatment with the compound of formula I and a compound of formula II at a rate of x+y kg of active ingredient.

If the activity actually observed is greater than the expected value We (factor observed activity/expected activity >1.2), there is a synergistic effect. The synergistic effect of the combinations of the active ingredient of AZO with the active ingredients described above is demonstrated in the following results.

Results

All rates below are expressed as mg ai/l (i.e. ppm).

| | Mixtures of azoxystrobin and fludioxonil | | | | | | | |
|---|---|---|---|---|---|---|---|---|
| | Fungus tested | Test | rate (AZO) | rate (FDL) | ratio | inh % (AZO alone) | inh % (FDL alone) | inh. % (combination) |
| AZO + FDL | A. tenuissima | 006-2005 | 100 | 0.2 | 500 | 30 | 70 | 100 |
| AZO + FDL | A. tenuissima | 006-2005 | 0.8 | 0.2 | 4 | 10 | 70 | 90 |
| AZO + FDL | A. tenuissima | 006-2005 | 0.2 | 0.2 | 1 | 10 | 70 | 90 |
| AZO + FDL | A. tenuissima | 006-2005 | 0.05 | 0.2 | 0.25 | 10 | 70 | 90 |
| AZO + FDL | P. chrysogenum | 006-2005 | 100 | 0.05 | 2000 | 10 | 0 | 30 |
| AZO + FDL | P. chrysogenum | 006-2005 | 50 | 0.05 | 1000 | 10 | 0 | 30 |
| AZO + FDL | P. chrysogenum | 006-2005 | 12.5 | 0.05 | 250 | 10 | 0 | 30 |
| AZO + FDL | P. chrysogenum | 006-2005 | 3.12 | 0.05 | 62.4 | 10 | 0 | 30 |
| AZO + FDL | P. chrysogenum | 006-2005 | 1.6 | 0.05 | 32 | 10 | 0 | 30 |
| AZO + FDL | P. chrysogenum | 006-2005 | 0.8 | 0.05 | 16 | 10 | 0 | 30 |
| AZO + FDL | P. chrysogenum | 006-2005 | 50 | 0.2 | 250 | 10 | 50 | 70 |
| AZO + FDL | P. chrysogenum | 006-2005 | 12.5 | 0.2 | 62.5 | 10 | 50 | 70 |
| AZO + FDL | P. chrysogenum | 006-2005 | 3.12 | 0.2 | 15.6 | 10 | 50 | 70 |
| AZO + FDL | P. chrysogenum | 006-2005 | 0.8 | 0.2 | 4 | 10 | 50 | 70 |
| AZO + FDL | P. chrysogenum | 006-2005 | 0.2 | 0.2 | 1 | 0 | 50 | 70 |
| AZO + FDL | P. chrysogenum | 006-2005 | 0.05 | 0.2 | 0.25 | 10 | 50 | 70 |
| AZO + FDL | A. versicolor | 006-2005 | 1.6 | 0.05 | 32 | 30 | 10 | 90 |
| AZO + FDL | A. versicolor | 006-2005 | 0.8 | 0.05 | 16 | 30 | 10 | 90 |
| AZO + FDL | A. niger | 006-2005 | 0.05 | 0.2 | 0.25 | 10 | 50 | 70 |
| AZO + FDL | A. niger | 006-2005 | 0.05 | 0.8 | 0.0625 | 10 | 70 | 90 |
| AZO + FDL | A. niger | 006-2005 | 0.05 | 1.6 | 0.031 | 10 | 70 | 90 |
| AZO + FDL | A. niger | 006-2005 | 0.05 | 3.12 | 0.016 | 10 | 70 | 90 |

-continued

| | Mixtures of azoxystrobin and fludioxonil | | | | | | | |
|---|---|---|---|---|---|---|---|---|
| | Fungus tested | Test | rate (AZO) | rate (FDL) | ratio | inh % (AZO alone) | inh % (FDL alone) | inh. % (combination) |
| AZO + FDL | A. niger | 006-2005 | 0.05 | 12.5 | 0.004 | 10 | 70 | 90 |
| AZO + FDL | A. tenuissima | 015-2005 | 100 | 100 | 1 | 10 | 70 | 100 |
| AZO + FDL | A. tenuissima | 015-2005 | 50 | 50 | 1 | 10 | 70 | 100 |
| AZO + FDL | A. tenuissima | 015-2005 | 25 | 25 | 1 | 10 | 70 | 100 |
| AZO + FDL | A. tenuissima | 015-2005 | 12.5 | 12.5 | 1 | 10 | 70 | 100 |
| AZO + FDL | A. tenuissima | 015-2005 | 6.25 | 6.25 | 1 | 10 | 50 | 100 |
| AZO + FDL | A. tenuissima | 015-2005 | 3.1 | 3.1 | 1 | 10 | 50 | 100 |
| AZO + FDL | A. tenuissima | 015-2005 | 1.6 | 1.6 | 1 | 10 | 50 | 100 |
| AZO + FDL | A. tenuissima | 015-2005 | 0.8 | 0.8 | 1 | 10 | 30 | 100 |
| AZO + FDL | A. tenuissima | 015-2005 | 0.4 | 0.4 | 1 | 10 | 30 | 70 |
| AZO + FDL | A. tenuissima | 015-2005 | 100 | 200 | 0.5 | 10 | 50 | 100 |
| AZO + FDL | A. tenuissima | 015-2005 | 50 | 100 | 0.5 | 10 | 70 | 100 |
| AZO + FDL | A. tenuissima | 015-2005 | 25 | 50 | 0.5 | 10 | 70 | 100 |
| AZO + FDL | A. tenuissima | 015-2005 | 12.5 | 25 | 0.5 | 10 | 70 | 100 |
| AZO + FDL | A. tenuissima | 015-2005 | 6.25 | 12.5 | 0.5 | 10 | 70 | 100 |
| AZO + FDL | A. tenuissima | 015-2005 | 3.1 | 6.25 | 0.49 | 10 | 50 | 100 |
| AZO + FDL | A. tenuissima | 015-2005 | 1.6 | 3.1 | 0.51 | 10 | 50 | 100 |
| AZO + FDL | A. tenuissima | 015-2005 | 0.8 | 1.6 | 0.5 | 10 | 50 | 100 |
| AZO + FDL | A. tenuissima | 015-2005 | 0.4 | 0.8 | 0.5 | 10 | 30 | 100 |
| AZO + FDL | A. tenuissima | 015-2005 | 200 | 100 | 2 | 10 | 70 | 100 |
| AZO + FDL | A. tenuissima | 015-2005 | 100 | 50 | 2 | 10 | 70 | 100 |
| AZO + FDL | A. tenuissima | 015-2005 | 50 | 25 | 2 | 10 | 70 | 100 |
| AZO + FDL | A. tenuissima | 015-2005 | 25 | 12.5 | 2 | 10 | 70 | 100 |
| AZO + FDL | A. tenuissima | 015-2005 | 12.5 | 6.25 | 2 | 10 | 50 | 100 |
| AZO + FDL | A. tenuissima | 015-2005 | 6.25 | 3.1 | 2.01 | 10 | 50 | 100 |
| AZO + FDL | A. tenuissima | 015-2005 | 3.1 | 1.6 | 1.93 | 10 | 50 | 100 |
| AZO + FDL | A. tenuissima | 015-2005 | 1.6 | 0.8 | 2 | 10 | 30 | 100 |
| AZO + FDL | A. tenuissima | 015-2005 | 0.8 | 0.4 | 2 | 10 | 30 | 70 |
| AZO + FDL | A. tenuissima | 015-2005 | 200 | 50 | 4 | 10 | 70 | 100 |
| AZO + FDL | A. tenuissima | 015-2005 | 100 | 25 | 4 | 10 | 70 | 100 |
| AZO + FDL | A. tenuissima | 015-2005 | 50 | 12.5 | 4 | 10 | 70 | 100 |
| AZO + FDL | A. tenuissima | 015-2005 | 25 | 6.25 | 4 | 10 | 50 | 100 |
| AZO + FDL | A. tenuissima | 015-2005 | 12.5 | 3.1 | 4.03 | 10 | 50 | 100 |
| AZO + FDL | A. tenuissima | 015-2005 | 6.25 | 1.6 | 3.90 | 10 | 50 | 100 |
| AZO + FDL | A. tenuissima | 015-2005 | 3.1 | 0.8 | 3.87 | 10 | 30 | 100 |
| AZO + FDL | A. tenuissima | 015-2005 | 1.6 | 0.4 | 4 | 10 | 30 | 100 |
| AZO + FDL | A. tenuissima | 015-2005 | 0.8 | 0.2 | 4 | 10 | 30 | 90 |

-continued

| | | Mixtures of azoxystrobin and fludioxonil | | | | | | |
|---|---|---|---|---|---|---|---|---|
| | Fungus tested | Test | rate (AZO) | rate (FDL) | ratio | inh % (AZO alone) | inh % (FDL alone) | inh. % (combination) |
| AZO + FDL | A. tenuissima | 015-2005 | 50 | 200 | 0.25 | 10 | 50 | 100 |
| AZO + FDL | A. tenuissima | 015-2005 | 25 | 100 | 0.25 | 10 | 70 | 100 |
| AZO + FDL | A. tenuissima | 015-2005 | 12.5 | 50 | 0.25 | 10 | 70 | 100 |
| AZO + FDL | A. tenuissima | 015-2005 | 6.25 | 25 | 0.25 | 10 | 70 | 100 |
| AZO + FDL | A. tenuissima | 015-2005 | 3.1 | 12.5 | 0.248 | 10 | 70 | 100 |
| AZO + FDL | A. tenuissima | 015-2005 | 1.6 | 6.25 | 0.256 | 10 | 50 | 100 |
| AZO + FDL | A. tenuissima | 015-2005 | 0.8 | 3.1 | 0.258 | 10 | 50 | 100 |

| | | Mixtures of azoxystrobin and thiabendazole | | | | | | |
|---|---|---|---|---|---|---|---|---|
| | Fungus tested | Test | rate (AZO) | rate (TBZ) | ratio | inh % (AZO alone) | inh % (TBZ alone) | inh. % (combination) |
| AZO + TBZ | A. tenuissima | 015-2005 | 200 | 200 | 1 | 30 | 0 | 100 |
| AZO + TBZ | A. tenuissima | 015-2005 | 100 | 100 | 1 | 30 | 0 | 100 |
| AZO + TBZ | A. tenuissima | 015-2005 | 50 | 50 | 1 | 30 | 0 | 100 |
| AZO + TBZ | A. tenuissima | 015-2005 | 25 | 25 | 1 | 30 | 0 | 50 |
| AZO + TBZ | A. tenuissima | 015-2005 | 100 | 200 | 0.5 | 30 | 0 | 100 |
| AZO + TBZ | A. tenuissima | 015-2005 | 50 | 100 | 0.5 | 30 | 0 | 100 |
| AZO + TBZ | A. tenuissima | 015-2005 | 25 | 50 | 0.5 | 30 | 0 | 100 |
| AZO + TBZ | A. tenuissima | 015-2005 | 200 | 100 | 2 | 30 | 0 | 100 |
| AZO + TBZ | A. tenuissima | 015-2005 | 100 | 50 | 2 | 30 | 0 | 100 |
| AZO + TBZ | A. tenuissima | 015-2005 | 50 | 25 | 2 | 30 | 0 | 100 |
| AZO + TBZ | A. tenuissima | 015-2005 | 25 | 12.5 | 2 | 30 | 0 | 50 |
| AZO + TBZ | A. tenuissima | 015-2005 | 50 | 200 | 0.25 | 30 | 0 | 100 |
| AZO + TBZ | A. tenuissima | 015-2005 | 25 | 100 | 0.25 | 30 | 0 | 100 |
| AZO + TBZ | A. tenuissima | 015-2005 | 12.5 | 50 | 0.25 | 30 | 0 | 100 |
| AZO + TBZ | A. tenuissima | 015-2005 | 200 | 50 | 4 | 30 | 0 | 100 |
| AZO + TBZ | A. tenuissima | 015-2005 | 100 | 25 | 4 | 30 | 0 | 100 |
| AZO + TBZ | A. tenuissima | 015-2005 | 50 | 12.5 | 4 | 30 | 0 | 100 |

| | | Mixtures of azoxystrobin and propiconazole | | | | | |
|---|---|---|---|---|---|---|---|
| | Fungus tested | Test | rate (AZO) | rate (PPZ) | ratio | inh % (AZO alone) | inh % (PPZ alone) | inh. % (combination) |
| AZO + PPZ | A. pullulans | 006-2005 | 0.2 | 3.12 | 0.064 | 10 | 70 | 90 |
| AZO + PPZ | A. pullulans | 006-2005 | 0.2 | 1.6 | 0.125 | 10 | 70 | 90 |
| AZO + PPZ | A. pullulans | 006-2005 | 0.8 | 12.5 | 0.064 | 10 | 70 | 90 |
| AZO + PPZ | A. pullulans | 006-2005 | 0.8 | 3.12 | 0.256 | 10 | 70 | 90 |
| AZO + PPZ | A. pullulans | 006-2005 | 0.8 | 1.6 | 0.5 | 10 | 70 | 90 |
| AZO + PPZ | A. pullulans | 006-2005 | 1.6 | 12.5 | 0.128 | 10 | 70 | 90 |

-continued

Mixtures of azoxystrobin and propiconazole

| | Fungus tested | Test | rate (AZO) | rate (PPZ) | ratio | inh % (AZO alone) | inh % (PPZ alone) | inh. % (combination) |
|---|---|---|---|---|---|---|---|---|
| AZO + PPZ | A. pullulans | 006-2005 | 1.6 | 3.12 | 0.512 | 10 | 70 | 90 |
| AZO + PPZ | A. pullulans | 006-2005 | 1.6 | 1.6 | 1 | 10 | 70 | 90 |
| AZO + PPZ | A. pullulans | 006-2005 | 3.12 | 12.5 | 0.249 | 10 | 70 | 100 |
| AZO + PPZ | A. pullulans | 006-2005 | 3.12 | 3.12 | 1 | 10 | 70 | 90 |
| AZO + PPZ | A. pullulans | 006-2005 | 3.12 | 1.6 | 1.95 | 10 | 70 | 90 |
| AZO + PPZ | A. pullulans | 006-2005 | 12.5 | 12.5 | 1 | 10 | 70 | 100 |
| AZO + PPZ | A. pullulans | 006-2005 | 12.5 | 3.12 | 4.006 | 10 | 70 | 90 |
| AZO + PPZ | S. chartarum | 006-2005 | 0.8 | 3.12 | 0.256 | 10 | 10 | 30 |
| AZO + PPZ | S. chartarum | 006-2005 | 0.8 | 1.6 | 0.5 | 10 | 10 | 30 |
| AZO + PPZ | S. chartarum | 006-2005 | 0.8 | 0.8 | 1 | 10 | 0 | 30 |
| AZO + PPZ | A. pullulans | 015-2005 | 50 | 50 | 1 | 0 | 70 | 100 |
| AZO + PPZ | A. pullulans | 015-2005 | 25 | 50 | 0.5 | 0 | 70 | 100 |
| AZO + PPZ | A. pullulans | 015-2005 | 100 | 50 | 2 | 0 | 70 | 100 |
| AZO + PPZ | A. pullulans | 015-2005 | 50 | 25 | 2 | 0 | 50 | 100 |
| AZO + PPZ | A. pullulans | 015-2005 | 12.5 | 50 | 0.25 | 0 | 70 | 100 |
| AZO + PPZ | A. pullulans | 015-2005 | 100 | 25 | 4 | 0 | 50 | 100 |

Mixtures of azoxystrobin and difenoconazole

| | Fungus tested | Test | rate (AZO) | rate (DFZ) | ratio | inh % (AZO alone) | inh % (DFZ alone) | inh. % (combination) |
|---|---|---|---|---|---|---|---|---|
| AZO + DFZ | A. pullulans | 006-2005 | 0.05 | 3.12 | 0.016 | 0 | 70 | 90 |
| AZO + DFZ | A. pullulans | 006-2005 | 0.2 | 3.12 | 0.064 | 10 | 70 | 90 |
| AZO + DFZ | A. pullulans | 006-2005 | 0.8 | 3.12 | 0.256 | 10 | 70 | 100 |
| AZO + DFZ | A. pullulans | 006-2005 | 1.6 | 3.12 | 0.512 | 10 | 70 | 100 |
| AZO + DFZ | A. pullulans | 006-2005 | 3.12 | 3.12 | 1 | 10 | 70 | 100 |
| AZO + DFZ | A. pullulans | 006-2005 | 12.5 | 3.12 | 4.006 | 10 | 70 | 100 |

Example 4

Mixtures of azoxystrobin, thiabendazole and fludioxonil
The following compounds and formulations were used:

| Active Ingredient (ai) | Abbreviation | Formulation |
|---|---|---|
| Fludioxonil | FDL | SC230 |
| Azoxystrobin | AZO | WG50 |
| Thiabendazole | TBZ | SC500 |

All compounds were tested at 8 rates, namely for 006-2005: (100, 50, 12.5, 3.1, 1.6, 0.8, 0.2, 0.05, 0 mg ai/l), for 015-2005: 200, 100, 25, 12.5, 6.25, 3.12, 1.6, 0.8, 0.4, 0.2 mg/l Test organisms and media used:

| Organism | Cultivation of fungi | Test medium | Test conditions |
|---|---|---|---|
| all organisms | 24° C., on PDA medium | spore suspension in 0.3% AE media | Incubation at 24° C. for 3-6 days |

Propagation of the different fungi:

For test 006-2005: *Alternaria tenuissima* (DSM 63360), *Penicillium chrysogenum* (DSM 895), *Cladosporium cladosporoides* (DSM62121), *Aspergillus niger* (DSM 63263), *Aspergillus versicolor* (DSM 1943) and *Aureobasidium pullulans* (ATCC 15233) were separately cultivated on PDA media to suppress sporulation. Spore suspensions were produced for each fungus. Spore concentrations of approx. 100,000 spores/ml were used.

For test 015-2006: *Alternaria tenuissima* (DSM 63360), *Penicillium pinophilum* (CBS342.61), *Gliocladium virens* (DSM1963), *Aspergillus niger* (DSM 63263), *Stachybotrys chartarum* (DSM 2144) and *Aureobasidium pullulans* (ATCC 15233) were separately cultivated on PDA media to suppress sporulation. Spore suspensions were produced for each fungus. Spore concentrations of approx. 100,000 spores/ml were used.

Test method used: liquid culture assay on 24 and 48 well plates respectively.

For testing of the 3 way mixtures each of the formulated fungicide (100 ul) was filled into the 24 and 48 well plates respectively. Afterwards 700 ul of 0.3% AE media was added to the plate. The spore suspension of the specific fungi was added to this media in advance containing approx. 100,000 spores/ml. For testing the solo compounds the equivalent of distilled water was added instead of the formulated fungicide volume of the mixing partners. The plates were then sealed and incubated at 24° C.

Dependent on the growth properties of each organisms, the evaluation was done after 3 to 6 days, when the surface of the check well was covered with mycelium. The evaluation was performed by assessing the growth of the fungi related to the check growth. The results are expressed as % activity relative to the check (values of 0-100% growth). Afterwards the results were converted in % growth inhibition.

Analysis:

For the mixtures of different fungicides the synergism was calculated based on the Colby equation, which is described above.

Results

All rates below are expressed as mg ai/l (i.e. ppm)

| | | | | | | | inh % (FDL | inh % (TBZ | |
|---|---|---|---|---|---|---|---|---|---|
| | Fungus tested | Test | rate (AZO) | rate (FDL) | rate (TBZ) | inh % (AZO alone) | alone) | alone) | inh. % (combination) |
| AZO + FDL + TBZ | A. tenuissima | 006-2005 | 100 | 0.2 | 0.2 | 10 | 50 | 0 | 70 |
| AZO + FDL + TBZ | A. tenuissima | 006-2005 | 50 | 0.2 | 0.2 | 10 | 50 | 0 | 70 |
| AZO + FDL + TBZ | A. tenuissima | 006-2005 | 12.5 | 0.2 | 0.2 | 10 | 50 | 0 | 70 |
| AZO + FDL + TBZ | A. tenuissima | 006-2005 | 3.12 | 0.2 | 0.2 | 10 | 50 | 0 | 70 |
| AZO + FDL + TBZ | A. tenuissima | 006-2005 | 1.6 | 0.2 | 0.2 | 10 | 50 | 0 | 70 |
| AZO + FDL + TBZ | A. tenuissima | 006-2005 | 0.8 | 0.2 | 0.2 | 10 | 50 | 0 | 70 |
| AZO + FDL + TBZ | A. tenuissima | 006-2005 | 0.2 | 0.2 | 0.2 | 10 | 50 | 0 | 70 |
| AZO + FDL + TBZ | A. tenuissima | 006-2005 | 0.05 | 0.2 | 0.2 | 10 | 50 | 0 | 70 |
| AZO + FDL + TBZ | A. tenuissima | 006-2005 | 100 | 0.8 | 0.8 | 10 | 70 | 0 | 100 |
| AZO + FDL + TBZ | A. tenuissima | 006-2005 | 50 | 0.8 | 0.8 | 10 | 70 | 0 | 100 |
| AZO + FDL + TBZ | A. tenuissima | 006-2005 | 12.5 | 0.8 | 0.8 | 10 | 70 | 0 | 100 |
| AZO + FDL + TBZ | A. tenuissima | 006-2005 | 3.12 | 0.8 | 0.8 | 10 | 70 | 0 | 100 |
| AZO + FDL + TBZ | A. tenuissima | 006-2005 | 1.6 | 0.8 | 0.8 | 10 | 70 | 0 | 100 |
| AZO + FDL + TBZ | A. tenuissima | 006-2005 | 0.8 | 0.8 | 0.8 | 10 | 70 | 0 | 100 |
| AZO + FDL + TBZ | A. tenuissima | 006-2005 | 0.2 | 0.8 | 0.8 | 10 | 70 | 0 | 100 |
| AZO + FDL + TBZ | A. tenuissima | 006-2005 | 0.05 | 0.8 | 0.8 | 10 | 70 | 0 | 100 |
| AZO + FDL + TBZ | A. tenuissima | 006-2005 | 100 | 1.6 | 1.6 | 10 | 70 | 0 | 100 |
| AZO + FDL + TBZ | A. tenuissima | 006-2005 | 50 | 1.6 | 1.6 | 10 | 70 | 0 | 100 |
| AZO + FDL + TBZ | A. tenuissima | 006-2005 | 12.5 | 1.6 | 1.6 | 10 | 70 | 0 | 100 |
| AZO + FDL + TBZ | A. tenuissima | 006-2005 | 3.12 | 1.6 | 1.6 | 10 | 70 | 0 | 100 |
| AZO + FDL + TBZ | A. tenuissima | 006-2005 | 1.6 | 1.6 | 1.6 | 10 | 70 | 0 | 100 |
| AZO + FDL + TBZ | A. tenuissima | 006-2005 | 0.8 | 1.6 | 1.6 | 10 | 70 | 0 | 100 |
| AZO + FDL + TBZ | A. tenuissima | 006-2005 | 0.2 | 1.6 | 1.6 | 10 | 70 | 0 | 100 |
| AZO + FDL + TBZ | A. tenuissima | 006-2005 | 0.05 | 1.6 | 1.6 | 10 | 70 | 0 | 100 |
| AZO + FDL + TBZ | A. versicolor | 006-2005 | 100 | 0.2 | 0.2 | 30 | 0 | 0 | 70 |
| AZO + FDL + TBZ | A. versicolor | 006-2005 | 50 | 0.2 | 0.2 | 30 | 0 | 0 | 70 |
| AZO + FDL + TBZ | A. versicolor | 006-2005 | 12.5 | 0.2 | 0.2 | 30 | 0 | 0 | 70 |
| AZO + FDL + TBZ | A. versicolor | 006-2005 | 3.12 | 0.2 | 0.2 | 30 | 0 | 0 | 70 |
| AZO + FDL + TBZ | A. versicolor | 006-2005 | 1.6 | 0.2 | 0.2 | 30 | 0 | 0 | 70 |
| AZO + FDL + TBZ | A. versicolor | 006-2005 | 0.8 | 0.2 | 0.2 | 30 | 0 | 0 | 70 |
| AZO + FDL + TBZ | A. versicolor | 006-2005 | 0.2 | 0.2 | 0.2 | 30 | 0 | 0 | 50 |
| AZO + FDL + TBZ | A. versicolor | 006-2005 | 0.05 | 0.2 | 0.2 | 10 | 0 | 0 | 30 |
| AZO + FDL + TBZ | A. versicolor | 006-2005 | 100 | 0.8 | 0.8 | 30 | 0 | 0 | 70 |
| AZO + FDL + TBZ | A. versicolor | 006-2005 | 50 | 0.8 | 0.8 | 30 | 0 | 0 | 70 |
| AZO + FDL + TBZ | A. versicolor | 006-2005 | 12.5 | 0.8 | 0.8 | 30 | 0 | 0 | 70 |
| AZO + FDL + TBZ | A. versicolor | 006-2005 | 3.12 | 0.8 | 0.8 | 30 | 0 | 0 | 70 |
| AZO + FDL + TBZ | A. versicolor | 006-2005 | 1.6 | 0.8 | 0.8 | 30 | 0 | 0 | 70 |

-continued

Test Number 006-2005

| | Fungus tested | Test | rate (AZO) | rate (FDL) | rate (TBZ) | inh % (AZO alone) | inh % (FDL alone) | inh % (TBZ alone) | inh. % (combination) |
|---|---|---|---|---|---|---|---|---|---|
| AZO + FDL + TBZ | A. versicolor | 006-2005 | 0.8 | 0.8 | 0.8 | 30 | 0 | 0 | 70 |
| AZO + FDL + TBZ | A. versicolor | 006-2005 | 0.2 | 0.8 | 0.8 | 30 | 0 | 0 | 30 |
| AZO + FDL + TBZ | A. versicolor | 006-2005 | 0.05 | 0.8 | 0.8 | 10 | 0 | 0 | 30 |
| AZO + FDL + TBZ | A. versicolor | 006-2005 | 100 | 1.6 | 1.6 | 30 | 0 | 10 | 100 |
| AZO + FDL + TBZ | A. versicolor | 006-2005 | 50 | 1.6 | 1.6 | 30 | 0 | 10 | 100 |
| AZO + FDL + TBZ | A. versicolor | 006-2005 | 12.5 | 1.6 | 1.6 | 30 | 0 | 10 | 100 |
| AZO + FDL + TBZ | A. versicolor | 006-2005 | 3.12 | 1.6 | 1.6 | 30 | 0 | 10 | 100 |
| AZO + FDL + TBZ | A. versicolor | 006-2005 | 1.6 | 1.6 | 1.6 | 30 | 0 | 10 | 100 |
| AZO + FDL + TBZ | A. versicolor | 006-2005 | 0.8 | 1.6 | 1.6 | 30 | 0 | 10 | 100 |
| AZO + FDL + TBZ | A. versicolor | 006-2005 | 0.2 | 1.6 | 1.6 | 30 | 0 | 10 | 100 |
| AZO + FDL + TBZ | A. versicolor | 006-2005 | 0.05 | 1.6 | 1.6 | 10 | 0 | 10 | 100 |
| AZO + FDL + TBZ | A. niger | 006-2005 | 0.05 | 0.8 | 0.8 | 10 | 50 | 0 | 90 |

Test Number 015-2005

| | Fungus tested | Test | rate (AZO) | rate (FDL) | rate (TBZ) | inh % (AZO alone) | inh % (FDL alone) | inh % (TBZ alone) | inh. % (combination) |
|---|---|---|---|---|---|---|---|---|---|
| AZO + FDL + TBZ | A. niger | 015-2005 | 0.05 | 0.8 | 0.8 | 0 | 50 | 0 | 70 |
| AZO + FDL + TBZ | A. niger | 015-2005 | 0.05 | 0.8 | 0.2 | 0 | 50 | 0 | 70 |
| AZO + FDL + TBZ | A. niger | 015-2005 | 0.05 | 1.6 | 0.8 | 0 | 50 | 0 | 70 |
| AZO + FDL + TBZ | A. niger | 015-2005 | 0.05 | 1.6 | 0.2 | 0 | 50 | 0 | 70 |
| AZO + FDL + TBZ | A. niger | 015-2005 | 0.05 | 3.1 | 0.8 | 0 | 50 | 0 | 70 |
| AZO + FDL + TBZ | A. niger | 015-2005 | 0.05 | 3.1 | 0.2 | 0 | 50 | 0 | 70 |
| AZO + FDL + TBZ | A. tenuissima | 015-2005 | 0.05 | 0.8 | 100 | 10 | 50 | 0 | 100 |
| AZO + FDL + TBZ | A. tenuissima | 015-2005 | 0.05 | 0.8 | 25 | 10 | 50 | 0 | 100 |
| AZO + FDL + TBZ | A. tenuissima | 015-2005 | 0.05 | 0.8 | 6.25 | 10 | 50 | 0 | 100 |
| AZO + FDL + TBZ | A. tenuissima | 015-2005 | 0.05 | 0.8 | 3.1 | 10 | 50 | 0 | 100 |
| AZO + FDL + TBZ | A. tenuissima | 015-2005 | 0.05 | 0.8 | 1.6 | 10 | 50 | 0 | 90 |
| AZO + FDL + TBZ | A. tenuissima | 015-2005 | 0.05 | 0.8 | 0.2 | 10 | 50 | 0 | 90 |
| AZO + FDL + TBZ | A. tenuissima | 015-2005 | 0.05 | 1.6 | 100 | 10 | 50 | 0 | 100 |
| AZO + FDL + TBZ | A. tenuissima | 015-2005 | 0.05 | 1.6 | 25 | 10 | 50 | 0 | 100 |
| AZO + FDL + TBZ | A. tenuissima | 015-2005 | 0.05 | 1.6 | 6.25 | 10 | 50 | 0 | 100 |
| AZO + FDL + TBZ | A. tenuissima | 015-2005 | 0.05 | 1.6 | 3.1 | 10 | 50 | 0 | 100 |
| AZO + FDL + TBZ | A. tenuissima | 015-2005 | 0.05 | 1.6 | 1.6 | 10 | 50 | 0 | 100 |
| AZO + FDL + TBZ | A. tenuissima | 015-2005 | 0.05 | 1.6 | 0.2 | 10 | 50 | 0 | 100 |
| AZO + FDL + TBZ | A. tenuissima | 015-2005 | 0.2 | 0.8 | 100 | 10 | 50 | 0 | 90 |

-continued

Test Number 015-2005

| | Fungus tested | Test | rate (AZO) | rate (FDL) | rate (TBZ) | inh % (AZO alone) | inh % (FDL alone) | inh % (TBZ alone) | inh. % (combination) |
|---|---|---|---|---|---|---|---|---|---|
| AZO + FDL + TBZ | A. tenuissima | 015-2005 | 0.2 | 0.8 | 25 | 10 | 50 | 0 | 90 |
| AZO + FDL + TBZ | A. tenuissima | 015-2005 | 0.2 | 0.8 | 6.25 | 10 | 50 | 0 | 100 |
| AZO + FDL + TBZ | A. tenuissima | 015-2005 | 0.2 | 0.8 | 3.1 | 10 | 50 | 0 | 100 |
| AZO + FDL + TBZ | A. tenuissima | 015-2005 | 0.2 | 0.8 | 1.6 | 10 | 50 | 0 | 100 |
| AZO + FDL + TBZ | A. tenuissima | 015-2005 | 0.2 | 0.8 | 0.2 | 10 | 50 | 0 | 100 |
| AZO + FDL + TBZ | A. tenuissima | 015-2005 | 0.2 | 1.6 | 100 | 10 | 50 | 0 | 100 |
| AZO + FDL + TBZ | A. tenuissima | 015-2005 | 0.2 | 1.6 | 25 | 10 | 50 | 0 | 100 |
| AZO + FDL + TBZ | A. tenuissima | 015-2005 | 0.2 | 1.6 | 6.25 | 10 | 50 | 0 | 100 |
| AZO + FDL + TBZ | A. tenuissima | 015-2005 | 0.2 | 1.6 | 3.1 | 10 | 50 | 0 | 100 |
| AZO + FDL + TBZ | A. tenuissima | 015-2005 | 0.2 | 1.6 | 1.6 | 10 | 50 | 0 | 100 |
| AZO + FDL + TBZ | A. tenuissima | 015-2005 | 0.2 | 1.6 | 0.2 | 10 | 50 | 0 | 100 |
| AZO + FDL + TBZ | S. chartarum | 015-2005 | 0.8 | 0.05 | 25 | 10 | 10 | 30 | 100 |
| AZO + FDL + TBZ | S. chartarum | 015-2005 | 0.8 | 0.05 | 6.25 | 10 | 10 | 10 | 100 |
| AZO + FDL + TBZ | S. chartarum | 015-2005 | 0.8 | 0.05 | 3.1 | 10 | 10 | 0 | 100 |
| AZO + FDL + TBZ | S. chartarum | 015-2005 | 1.6 | 0.05 | 6.25 | 10 | 10 | 10 | 100 |
| AZO + FDL + TBZ | S. chartarum | 015-2005 | 1.6 | 0.05 | 3.1 | 10 | 10 | 10 | 100 |
| AZO + FDL + TBZ | S. chartarum | 015-2005 | 3.1 | 0.2 | 25 | 30 | 50 | 30 | 100 |
| AZO + FDL + TBZ | S. chartarum | 015-2005 | 3.1 | 0.2 | 6.25 | 30 | 50 | 10 | 100 |
| AZO + FDL + TBZ | S. chartarum | 015- | 3.1 | 0.2 | 3.1 | 30 | 50 | 0 | 100 |

Example 5

Hand sheets efficacy testing
Preparation of the hand sheets:
The hand sheets are made using 80% OCC pulp concentrate (old corrugated cartons)+20% ONP (old newspapers) pulp concentrate plus additional ingredients. The fungicides are added during preparation by mixing and then the hand sheets are dried.
The following compounds and formulations may be used:

| Active Ingredient (ai) | Abbreviation | Formulation |
|---|---|---|
| Fludioxonil | FDL | 4FS |
| Azoxystrobin | AZO | SC250 |
| Thiabendazole | TBZ | MP340 |

For efficacy testing the test organisms are cultivated separately on PDA media to suppress sporulation. Spore suspensions are produced for each fingi (spore concentrations of approximately $10^6$/ml). Organisms which may be used include Chaetomium globosum (ATCC 6205), Penicillium citrinum (ATCC 9849), Stachybotrys chartarum (ATCC16026) and Aspergillus niger (DSM 6275) as pure culture but also as mixed inoculum.
Mineral agar (according to ASTM G21-96) can be used as test media. Before inoculation the hand sheets are divided in 5 pieces each, each piece is placed in a separate dish and then inoculated with the fungi. The samples are then incubated at 30° C. for 28 days. Pre-reading of the samples may be performed at approximately 10 days after inoculation. The activity of the treatments may be assessed visually, using a rating system of 0-100% growth inhibition of fungal growth. For the mixtures of different fungicides the synergism can be calculated based on the Colby equation, which is described above.

The invention claimed is:

1. A wallboard that has been treated with a fungicidally effective amount of a composition consisting of, as active ingredients, synergistic amounts of the fungicides (a) azoxystrobin, (b) thiabendazole, and (c) fludioxonil.

2. Wallboard according to claim 1 wherein the fungicides are included in the gypsum core.

3. Wallboard according to claim 1 wherein the fungicides are included in the paper coating of the wallboard.

4. Wallboard according to claim 1 wherein the fungicides are applied after the wallboard is made.

5. Wallboard according to claim 1, wherein the fungicides are on an outer surface of the gypsum core.

6. A method for the prevention and/or treatment of growth and/or infestation of a fungus on a wallboard comprising treating the wallboard with a composition consisting of, as active ingredients, synergistic amounts of the fungicides (a) azoxystrobin, (b) thiabendazole, and (c) fludioxonil.

* * * * *